United States Patent [19]

Pesa et al.

[11] 4,451,407

[45] * May 29, 1984

[54] CARBONYLATION OF OLEFINICALLY UNSATURATED COMPOUNDS

[75] Inventors: Frederick A. Pesa, Aurora; Thomas A. Haase, University Heights, both of Ohio

[73] Assignee: The Standard Oil Company, Cleveland, Ohio

[*] Notice: The portion of the term of this patent subsequent to May 25, 1999 has been disclaimed.

[21] Appl. No.: 332,059

[22] Filed: Dec. 18, 1981

Related U.S. Application Data

[63] Continuation of Ser. No. 170,308, Jul. 16, 1980, Pat. No. 4,331,612, which is a continuation-in-part of Ser. No. 973,069, Dec. 28, 1978, abandoned.

[51] Int. Cl.$^3$ .................. C07C 120/00; C07C 121/16
[52] U.S. Cl. .............................. 260/465.4; 260/465.1; 260/465.6; 260/465.8 R; 560/233; 562/522; 568/455; 549/295
[58] Field of Search .............. 260/465.4, 465.1, 465.6

[56] References Cited

U.S. PATENT DOCUMENTS

| | | | |
|---|---|---|---|
| 2,820,059 | 1/1958 | Hasek et al. ................. | 260/604 HF |
| 2,964,558 | 12/1960 | Leathers et al. ................... | 560/206 |
| 3,010,994 | 11/1961 | Iwanaga et al. ............. | 260/465.1 X |
| 3,060,228 | 10/1962 | Pino ..................... | 560/206 |
| 3,257,459 | 6/1966 | Swakon et al. ............. | 260/604 HF |
| 3,334,132 | 8/1967 | Landis ..................... | 560/206 |
| 3,373,107 | 3/1968 | Rice et al. ...................... | 260/583 D |
| 3,734,963 | 5/1973 | Langer et al. ............. | 260/583 D X |
| 3,818,060 | 6/1974 | Forster .................... | 562/522 X |
| 3,931,332 | 1/1976 | Wilkes ..................... | 260/604 HF |
| 3,935,228 | 1/1976 | Keblys ..................... | 260/604 HF X |
| 3,946,055 | 3/1976 | Isa et al. ........................ | 560/233 X |
| 3,996,164 | 12/1976 | Matsuda ................... | 260/604 HF X |
| 4,041,057 | 8/1977 | Fanning ........................ | 560/233 X |
| 4,060,543 | 11/1977 | Weitz et al. ................. | 260/465.4 X |
| 4,141,915 | 2/1979 | El-Chahawi et al. ........... | 260/465.4 |
| 4,153,795 | 5/1979 | Matsuda .................... | 260/604 HF X |
| 4,189,448 | 2/1980 | Carlock ........................ | 560/455 X |
| 4,209,467 | 6/1980 | Kojima et al. .................. | 560/233 X |
| 4,331,612 | 5/1982 | Pesa et al. ....................... | 260/465.4 |

FOREIGN PATENT DOCUMENTS

2000153 1/1979 United Kingdom .
2028677A 3/1980 United Kingdom .

OTHER PUBLICATIONS

Brause, et al., J.A.C.S., 89, (1967), pp. 6500-6502.
Wayman, et al., J.A.C.S., 89 (1967), pp. 3135-3141.
Falbe, "Carbon Monoxide in Organic Synthesis", 1970, (Springer-Verlag, N.Y.), pp. 19, 52-55, 113, 157.
Smith, "The Chemistry of Open Chain Organic Nitrogen Compounds", vol. II, (1966), pp. 21-22.
Millar, et al., "Sidgwick's Organic Chemistry of Nitrogen", 3rd ed., (1966), pp. 134-135.

*Primary Examiner*—Joseph Paul Brust
*Attorney, Agent, or Firm*—Thomas P. Schur; Joseph G. Curatolo; Larry W. Evans

[57] ABSTRACT

Oxygenated organic compounds, e.g. esters, aldehydes, and amides, are prepared by reacting an olefinically unsaturated compound with carbon monoxide and a compound containing a replaceable hydrogen atom in the presence of a catalyst comprising cobalt or ruthenium carbonyl and a promoter ligand. The promoter ligand is selected from the group consisting of heterocyclic nitrogen oxide compounds and phosphorus or sulfur oxides. These reactions are carried out under relatively mild conditions of temperature and pressure.

21 Claims, No Drawings

CARBONYLATION OF OLEFINICALLY UNSATURATED COMPOUNDS

CROSS-REFERENCE TO RELATED APPLICATIONS

This application is a continuation of co-pending U.S. Ser. No. 170,308 filed July 16, 1980, which issued May 25, 1982, as U.S. Pat. No. 4,331,612, which is a continuation-in-part of U.S. Ser. No. 973,069, filed Dec. 28, 1978, now abandoned.

BACKGROUND OF THE INVENTION

The present invention relates to a novel process for producing oxygenated organic compounds.

There are several known methods for producing oxygenated organic compounds. The acid catalyzed ($H_2SO_4$, $HBF_4$, etc.) synthesis of carboxylic acids or esters by the reaction of an olefinic substrate with CO and water or alcohol has been known since 1931. (J. Falbe, "Carbon Monoxide in Organic Synthesis", Springer-Verlag, New York (1970)). Although this process was used on a commercial scale it does have serious limitations due to the reaction conditions and the isomeric composition of the products.

A more commercially important synthesis of carboxylic acid/esters is the direct carbonylation of olefinic substrates with CO and water/alcohol conducted in the presence of transition metals. In general, this carbonylation reaction, discovered by Repp in 1940 (I. Wender and P. Pino, "Organic Synthesis Via Metal Carbonyls", Volume 2, John Wiley, New York (1977)), involves the addition of carbon monoxide, carboxyl alkyl or amide group (Y—H where Y equals —Or or —NHR and R is an alkyl), and an olefin.

However, when an unsymmetrical olefin is used as the substrate at least two isomeric products are obtained. No general method has been developed for the control of the isomeric product composition.

The present invention overcomes some of these problems present in the prior art. For example, inventive process results in higher conversions, higher yields and faster reaction rates than those disclosed in the prior art. Furthermore, the instant process allows one to obtain a high yield of a particular isomeric product composition. Thus, extremely high selectivities of particular oxygenated organic compounds can be obtained by the inventive process.

Finally, the prior art carbonylation reactions oerate under extreme conditions of temperature and pressure. In general, temperature in the range of 160° C. to 300° C. and pressures in the range of 1,500 to 5,000 psi are required. On the other hand, the present reaction may be carried out under relatively mild conditions of temperature and pressure. This further advantage can result in substantial cost savings in the production of oxygenated organic compounds.

SUMMARY OF THE INVENTION

It has now been discovered that oxygenated organic compounds can be produced by contacting an olefinically unsaturated compound with carbon monoxide and a compound containing a replaceable hydrogen atom in the presence of a catalyst comprising cobalt and/or ruthenium carbonyl and a promotor ligand selected from the group consisting of heterocyclic nitrogen oxide compounds and phosphorus or sulfur oxides.

In particular, the inventive process results in high yields of oxygenated organic compounds when operating at much lower temperatures and pressure than disclosed in the prior art. In addition, the product distribution can be varied significantly by changing the $CO/H_2$ ratio, pressure, ligand, solvent, reaction time and other process variables.

Thus, the present invention provides a novel catalyst comprising a promoter ligand and at least one of cobalt and ruthenium carbonyl. Furthermore, the instant invention provides a novel process for the production of an oxygenated organic compound comprising contacting an olefinically unsaturated compound with carbon monoxide and a compound containing replaceable hydrogen atom in the presence of the above catalyst. Finally, the present invention provides a novel process for the production of an oxygenated organic compound comprising contacting an olefinically unsaturated compound containing an alcohol moiety with carbon monoxide in the presence of the above catalyst.

Specifically, the carbonylation reaction of acrylonitrile, carbon monoxide, hydrogen gas, and methanol to yield methyl-$\beta$-cyanopropionate proceeds smoothly using a catalyst comprising cobalt carbonyl and a heterocyclic nitrogen oxide promotor ligand.

DETAILED DESCRIPTION

According to the present invention, improved yields and selectivities of oxygengated organic compounds are obtained by contacting an olefinically unsaturated compound with carbon monoxide and a compound containing a replaceable hydrogen atom over a catalyst comprising cobalt and/or ruthenium carbonyl and a promoter ligand selected from the group consisting of heterocyclic nitrogen oxide compounds and phosphorus or sulfur oxides. The overall reaction taking place in this process is represented by the following equation:

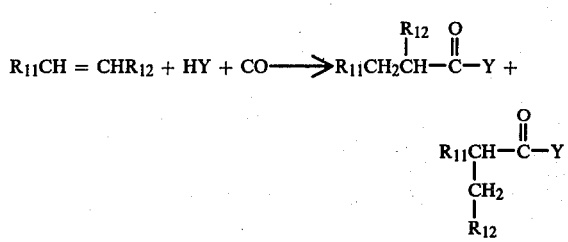

$R_{11}$, $R_{12}$ and Y are defined below.

Reactants

Olefinically unsaturated compounds which can be employed as reactants in the inventive process preferably have the following structure:

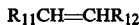

wherein $R_{11}$ and $R_{12}$ are each independently selected from:

(1) hydrogen (either $R_{11}$ or $R_{12}$ but not both);
(2) $C_{1-30}$ alkyl;
(3) —$(CH_2)_p$—CN, wherein p is 0-3;
(4) —$(CH_2)_q$—$OR_{13}$, wherein q is 1-30 and $R_{13}$ is hydrogen; methyl or ethyl; and
(5) —$(CH_2)_n$—$COOR_{17}$, wherein n is 0-5 and $R_{17}$ is hydrogen, methyl or ethyl.

Preferably, the olefinically unsaturated compounds comprise compounds wherein $R_{11}$ or $R_{12}$ are each independently selected from:
(1) hydrogen (either $R_{11}$ or $R_{12}$ but not both);
(2) $C_{1-10}$ alkyl;
(3) $-(CH_2)_p-CN$, wherein p is 0–2; and
(4) $-(CH_2)_q-OH$, wherein q is 1–10.

Most preferably, the olefinically unsaturated compounds comprise compounds wherein $R_{11}$ and $R_{12}$ are each independently selected from hydrogen (either $R_{11}$ or $R_{12}$ but not both), methyl and $-(CH_2)_p-CN$, wherein p is 0–1.

The second component in the inventive reaction system is a compound containing a replaceable hydrogen atom. This compound can be represented by the following formula:

$$H-Y$$

wherein Y is selected from the group consisting of:
(1) $OR_{14}$ wherein $R_{14}$ is a $C_{1-30}$ alkyl;
(2)

wherein $R_{15}$ and $R_{16}$ are each independently selected from $C_{1-10}$ alkyls; and
(3) H.

Preferably Y is selected from the group consisting of:
(1) $OR_{14}$ wherein $R_{14}$ is a $C_{1-10}$ alkyl;
(2)

wherein $R_{15}$ and $R_{16}$ are each independently selected from $C_{1-4}$ alkyls; and
(3) H.

More preferably Y is selected from the group consisting of:
(1) $OR_{14}$ wherein $R_{14}$ is a $C_{1-4}$ alkyl; and
(2) H.

The second component is most preferably either methanol or hydrogen.

In the embodiment of the invention in which H—Y is an alcohol or amine, it is preferred to add hydrogen gas to the reaction system. Preferably the amount of hydrogen gas so added comprises less than 10% by volume of the total amount of the hydrogen gas and carbon monoxide gas in the reaction system. More preferably the hydrogen gas comprises 0.5% to 7.5% by volume of the hydrogen and carbon monoxide gas. The addition of hydrogen gas can increase both the yield and selectivity to desired products in this mode of the invention.

When $H_2$ is compound containing a replaceable hydrogen atom then the reaction system will preferably contain 10% to 60% by volume hydrogen gas based on the total volume of the carbon monoxide and hydrogen gas. More preferably the reaction system will contain about 50% hydrogen gas.

One way to supply carbon monoxide and hydrogen gas into the reaction system is in the form of synthesis gas. The amount of hydrogen in the synthesis gas can be easily adjusted prior to insertion into the reactor.

The amount of carbon monoxide in the reaction system is not critical. Preferably the carbon monoxide is present in at least stoichiometric amounts and most preferably the carbon monoxide is present in amounts greatly in excess of stoichiometric amounts. If desired, a carrier gas which is inert to the reactants, products and catalyst can be included in the reaction system.

The molar ratio of the compound containing a replaceable hydrogen atom to the olefinically unsaturated compound can be 0.5–100:1 with a ratio of 1–10:1 being preferred. This ratio does not include the hydrogen gas which may be added to the reaction system when H—Y is an alcohol or amine.

In the embodiment of the invention in which the olefin reactant is an alcohol (i.e. wherein $R_{11}$ or $R_{12}$ is $-(CH_2)_q-OH$), it has been found that the terminal hydrogen atom on the alcohol group will itself serve as a replaceable hydrogen atom. As a result, the alcohol moeity of the olefin will react with the olefinic double bond of the olefin thereby producing a lactone. In this reaction system no H—Y component need be included since the olefin itself acts both as the olefin and the H—Y component. The reaction in this particular system is shown by the following equation:

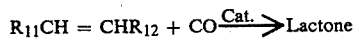

wherein at least one of $R_{11}$ and $R_{12}$ is an alcohol.

Process Conditions

Generally, in carrying out the inventive process, the olefinically unsaturated compound, carbon monoxide, and the compound containing a replaceable hydrogen atom are contacted with one another in the liquid phase in the presence of the catalyst described below. The inventive reaction can be accomplished in the batch mode or continuously.

The reaction temperature is normally maintained between 50° C. to 150° C. and most preferably at about 100° C. The reaction pressure is normally maintained at 100 to 2500 psi, preferably at 700 to 1000 psi. When the reaction is carried out in a batch mode, the reactants and catalysts are contacted with one another for a period of ten minutes through six hours, and preferably one half hour to four hours. A reaction time of less than ten minutes or more than six hours can be used if desired although better results will be obtained if the reaction time is maintained within this range. When the process is carried out on a continuous basis, the reaction catalyst contact time is normally 10 seconds to 10 minutes, preferably 100 seconds to 5 minutes.

Both the rate of reaction and product distribution can be varied significantly by changing the process parameters. For example, normally an increase in pressure increases the rate of reaction. However, at very high pressures the reaction rate may decrease due to catalyst decomposition. Furthermore, the selectivity to a particular product may be affected by pressure changes, e.g. in the carbonylation of acrylonitrile there is an increase in the selectively to the n-cyanoester (3CE) as the pressure decreases.

A balance exists between temperature and pressure with respect to catalyst decomposition. Generally, as the temperature increases the rate of reaction increases. However, an anomolous effect may occur due to partial catalyst decomposition. Thus, the temperature and pressure must be carefully adjusted.

Similarly, residence time has a large effect on homogeneous processes. For example, in the process for the carbonylation of acrylonitrile, the selectivity to methly-β-cyanopropionate is much higher at short reaction times. Applicants surmise that the reduction in selectivity as a function of reaction time is caused by the reduction of the ligand, e.g. ;b 4-picoline-N-oxide is reduced to 4-picoline. In view of the above discussion, it is clear that a particular reaction rate and product distribution can be obtained by a careful adjustment of the process variables.

Catalysts

The catalyst employed in the inventive process can be generally described as one of two types. Both types comprise cobalt and/or ruthenium carbonyl and a promoter ligand in an organic solvent. The promoter ligand is either a heterocyclic nitrogen oxide compound or a phosphorus or sulfur oxide.

The nitrogen heterocyclic promoter ligand has the following structure:

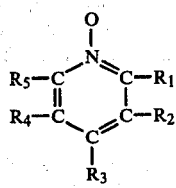

wherein $R_1$, $R_2$, $R_3$, $R_4$, and $R_5$ are each independently selected from the group consisting of:
(1) H;
(2) $C_{1-10}$ alkyls;
(3) $(CH_2)_qOH$ wherein q is 0–10;
(4)

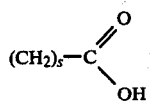

wherein s is 0–10; and
(5) $O(CH_2)_tCH_3$ wherein t is 0–10;
wherein $R_1$ and $R_2$ may comprise a five to eight membered carbocyclic fused ring optionally substituted with $C_{1-10}$ alkyls.

Preferably, $R_1$, $R_2$, $R_3$, $R_4$, and $R_5$ are selected from H, $C_{1-4}$ alkyls, $CH_2OH$, OH,

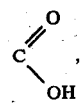

and $OCH_3$. Most preferably, $R_1$, $R_2$, $R_3$, $R_4$, and $R_5$ are selected from H, $CH_3$, and $OCH_3$.

The phosphorus or sulfur oxide promoter ligands have the following formula:

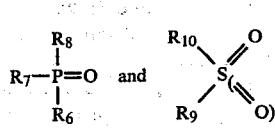

wherein $R_6$, $R_7$, $R_8$, $R_9$, and $R_{10}$ are each independently selected from:
(1) $C_{1-10}$ alkyls;
(2) polynuclear aryls containing up to 12 carbon atoms, optionally substituted with $C_{1-10}$ alkyls; and
(3) $O(CH_2)_tCH_3$, wherein t is 0–10; and
wherein n is 0 or 1.

Preferably, $R_6$, $R_7$, $R_8$, $R_9$, and $R_{10}$ are each independently selected from $C_{1-4}$ alkyls and most preferably $R_6$, $R_7$, $R_8$, $R_9$, and $R_{10}$ are $CH_3$.

The inventive catalyst can be prepared by mixing the cobalt and/or ruthenium carbonyl with at least one promoter ligand in a solvent. The cobalt and/or ruthenium carbonyl and the promoter ligand may be added simultanteously or separately to he solvent. The exact relationship in the solvent between the cobalt and/or ruthenium carbonyl and the promoter ligand is not know.

Any organic solvent in which the catalyst is soluble and which does not adversely affect the carbonylation reaction may be used in the present invention. Preferably, the solvent is an alcoholic, aromatic, ester, nitrile and/or dinitrile. The solvent is most preferably an alcohol or ester. In fact, the alcohol can be both a compound containing a replaceable hydrogen atom described above and the solvent. The preferred catalyst concentration in the solvent is normally between 0.1% to 5% by weight.

The cobalt and/or ruthenium carbonyl can be added to the solvent in any form from which cobalt and/or ruthenium carbonyl could be formed. For example, it is well known in the art that carbonyls can be formed from naphthenates, salts and nitrates and thus suitable naphthenates, salts and nitrates can be added to the solvent to form a carbonyl compound in situ. Preferably, the catalyst contains cobalt carbonyl.

In general, the promoter ligand to cobalt and/or ruthenium carbonyl molar ratio is 0.1–50:1, preferably about 0.5–4, and most preferably about 2:1. This ratio will vary depending on the promoter ligand chosen. At high ligand to carbonyl ratios (i.e. 4:1) the rate of reaction substantially decreases even though selectivity to the desired product can be increased. Thus, in the carbonylation of acrylonitrile, at high ligand/carbonyl ratios the reaction rate decreases but the selectivity to methyl-β-cyanopropionate increases.

The catalyst of this invention is dissolved in the reaction medium as a homogeneous catalyst. These homogeneous catalysts are prepared by known techniques. Specific preparations of these catalysts are shown in the working examples of this specification. Broadly, however, the catalysts of this invention can be prepared by any of the techniques known in the art.

Recovery

The reaction product obtained upon completion of the reaction is normally in the form of a liquid and composed primarily of unreacted reactants, catalyst and oxygenated organic compounds. This reaction product can be subjected to suitable known separation techniques, i.e. solvent extraction and fractional distillation, to yield the desired end products.

A particularly good method for separating the catalyst from the products obtained in the present process is by the use of conjugate phase extraction. In this separation scheme, the reaction effluent is treated with a $C_5$ to $C_8$ hydrocarbon which is miscible with the reaction solvent but which is a very poor solvent for the catalyst.

Examples of such hydrocarbons are pentane, hexane and octane. Enough of this hydrocarbon is added to the reactor effluent to separate almost all of the catalyst into one phase and a significant amount of products into the other phase. Generally, this is between 1 to 4 volumes of hydrocarbon per volume of reactor effluent.

It is desirable to exclude oxygen from this separation system so that catalyst decomposition will not occur. It is also desirable to minimize the amounts of unreacted substrates in reactor effluent prior to treatment with the hydrocarbon. This can be accomplished by simple distillation or vacuum stripping. Finally, it is desirable to separate the products and reactants as quickly as possible to reduce the possibility of unwanted side reactions, e.g. methyl-$\beta$-cyanopropionate reacts with acrylonitrile to produce a dicyano ester.

The catalyst containing hydrocarbon phase can be diluted and recycled back to the reactor. The product phase is then subjected to known separation techniques such as distillation or extraction.

The oxygenated organic compounds produced by this process are useful as precursors to polymers. The esters are also useful in perfumes, flavorings and pharmaceuticals. The aldehydes are useful as plasticizers and as intermediates for alcohols.

SPECIFIC EMBODIMENTS

In order to more thoroughly illustrate the present invention, the following working examples are presented. In these examples, the following definitions are used:

$$\% \text{ Conv} = \frac{\text{moles carbon in reactant converted to product}}{\text{moles carbon in reactant fed}} \times 100$$

$$\% \text{ Yield} = \frac{\text{moles carbon of olefinically unsaturated compound converted to product}}{\text{moles carbon of olefinically unsaturated compound fed}} \times 100$$

The results have all been adjusted to a 100% carbon balance.

In general, the experimental method consists of placing a pre-weighed solution of olefinically unsaturated compound, promoter ligand, compound containing a replaceable hydrogen atom and solvent into a glasslined autoclave. Next, cobalt carbonyl, $Co_2(CO)_8$, is added and the autoclave sealed.

The autoclave is flushed two times with synthesis gas and then charged with the synthesis gas to the desired pressure. The temperature is then incresed and the reaction proceeds for 1 to 4 hours. Occasionally, samples are withdrawn during the course of the reaction through the vent tube and subjected to gas chromatography analysis. After the runs, the glasslined autoclave is brought to room temperature by cooling with cold water, depressurized and opened for product analysis.

The results of the experiments are shown in Table I. A glossery of terms follows Table I and specifies the meanings of the abbreviations used in Table I.

EXAMPLE 1

13.5 gms. of acrylonitrile, 0.88 gms. of 4-picoline-N-oxide, 9.78 gms. of methanol and 100 mls. of adiponitrile were placed in a glasslined autoclave. Next, 1.37 gms. of $Co_2(CO)_8$ were added and the autoclave sealed.

The autoclave was charged with synthesis gas containing 5% $H_2$ until a pressure of 1,000 psi was reached. The temperature was set at 97.5° C. and the reaction proceeded for 90 minutes. The autoclave was then brought to room temperature by cooling with cold water, depressurized and opened for product analysis. The product analysis is shown in Table I.

EXAMPLE 2

13.5 gms of acrylonitrile, 0.88 gms. of 4-picoline-N-oxide and 100 mls. of methanol were placed in a glasslined autoclave. Next, 1.37 gms. of $Co_2(CO)_8$ were added and the autoclave sealed.

The autoclave was charged with synthesis gas containing 5% $H_2$ to a pressure of 1,000 psi. The temperature was set at 97.5° C. and the reaction proceeded for 150 minutes. The autoclave was then brought to room temperature by cooling with cold water, depressurized and opened for product analysis. The product analysis is shown in Table I.

EXAMPLE 3 THRU 80

The procedure outlined in Example 1 was followed with the molar ratio of cobalt carbonyl/ligand, temperature, pressure, solvent and reaction time being varied. These variables are specified in Table I for each example. Table I also shows the product analysis for Examples 3 thru 80.

EXAMPLE 81

13.5 gms. of acrylonitrile, 0.75 gms. of pyridine-N-oxide and 100 mls. of methanol were placed into a glasslined autoclave. Next, 1.37 gms. of $Co_2(CO)_8$ were added and the autoclave sealed.

The autoclave was charged with synthesis gas containing 5% $H_2$ to a pressure of 800 psi. The temperature was set at 95° C. and the reaction proceeded for 60 minutes. The glasslined autoclave was then brought to room temperature by cooling with cold water, depressurized and opened for product analysis. The product analysis is shown in Table I.

EXAMPLE 82

This example followed the same procedure outlined in Example 81 except that the temperature and reaction time were varied as set forth in Table I. The results are shown in Table I.

EXAMPLE 83

13.5 gms. of acrylonitirle, 0.88 gms. of 2-picoline-N-oxide and 100 mls. of methanol were placed in a glasslined autoclave. Next, 1.37 gms. of $Co_2(CO)_8$ were added and the autoclave sealed.

The autoclave was charged with synthesis gas containing b 5% $H_2$ to a pressure of 800 psi. The temperature was set at 95° C. and the reaction proceeded for 120 minutes. The glasslined autoclave was then brought to room temperature by cooling with cold water, depressurized and opened for product analysis. The product analysis is shown in Table I.

EXAMPLES 84 THRU 97

The procedure outlined in Example 83 was followed except that the molar ratio of cobalt carbonyl/ligand, solvent, ligand, temperature, pressure and reaction time were varied. These variables are specified in Table I for each example. Table I also shows the product analysis for Examples 84 thru 97.

TABLE I

CARBONYLATION WITH HETEROCYCLIC NITROGEN COMPOUNDS

Catalyst: $Co_2(CO)_8$ + Ligand  
Unsaturated Olefin Feed: Acrylonitrile

| Example | Ligand | $Co_2(CO)_8$/Ligand | Solvent | Temp (°C.) | Pres (psi) | Time (min) | Conv (%) | 3-CE | 2-CE | PN | 3-CPA | 3-CPAA | 3-MPN |
|---|---|---|---|---|---|---|---|---|---|---|---|---|---|
| 1 | 4-PcNox | 1:2 | ADN+MeOH | 97.5 | 1000 | 90 | 84.40 | 97.50 | — | — | — | — | 2.50 |
| 2 | 4-PcNox | 1:2 | MeOH | 97.5 | 1000 | 150 | 100.00 | 54.10 | 38.90 | 1.69 | — | 4.47 | — |
| 3 | 4-PcNox | 1:2 | ADN+MeOH | 97.5 | 1000 | 180 | 80.80 | 62.90 | 35.50 | — | — | — | 1.60 |
| 4 | 4-PcNox | 1:2 | MeOH | 75 | 800 | 180 | 100.00 | 40.10 | 57.60 | — | — | 0.78 | — |
| 5 | 4-PcNox | 1:2 | DMP+MeOH | 77.5 | 800 | 10 | 66.30 | 57.00 | 34.50 | 1.40 | — | 0.20 | 6.70 |
| 6 | 4-PcNox | 1:2 | DMP+MeOH | 77.5 | 800 | 60 | 100.00 | 52.40 | 41.10 | 0.90 | — | 1.50 | 4.20 |
| 7 | 4-PcNox | 1:2 | MeOH | 95 | 800 | 60 | 100.00 | 55.30 | 40.24 | 1.33 | — | 2.25 | — |
| 8 | 4-PcNox | 1:4 | MeOH | 95 | 800 | 60 | 100.00 | 51.26 | 45.98 | 1.16 | — | 0.64 | 0.61 |
| 9 | 4-PcNox | 1:1 | MeOH | 95 | 800 | 90 | 97.10 | 51.80 | 42.52 | 1.53 | — | 3.39 | — |
| 10 | 4-PcNox | 1:2 | DMP+MeOH | 97.5 | 800 | 15 | 98.60 | 53.40 | 40.80 | 0.62 | — | 0.23 | 4.90 |
| 11[1] | 4-PcNox | 1:2 | DMP+MeOH | 97.5 | 800 | 15 | 51.50 | 50.90 | 39.20 | 3.20 | — | — | 6.80 |
| 12[2] | 4-PcNox | 1:2 | DMP+MeOH | 97.5 | 800 | 20 | 99.50 | 47.40 | 33.80 | 1.90 | 11.23 | 1.73 | 3.90 |
| 13 | 4-PcNox | 1:2 | DMP+MeOH | 97.5 | 800 | 20 | 51.73 | 90.47 | — | — | — | — | 9.53 |
| 14 | 4-PcNox | 1:1 | DMP+MeOH | 97.5 | 800 | 25 | 99.90 | 40.50 | 40.50 | — | 8.80 | 6.80 | 0.32 |
| 15 | 4-PcNox | 1:2 | DMP+MeOH | 97.5 | 800 | 30 | 70.49 | 91.50 | — | — | — | — | 7.94 |
| 16 | 4-PcNox | 1:4 | DMP+MeOH | 97.5 | 800 | 35 | 99.10 | 52.30 | 38.70 | 0.50 | — | 0.40 | 8.10 |
| 17[1] | 4-PcNox | 1:2 | DMP+MeOH | 97.5 | 800 | 40 | 100.00 | 50.60 | 46.20 | — | — | — | 3.10 |
| 18[1] | 4-PcNox | 1:2 | DMP+MeOH | 97.5 | 800 | 45 | 99.95 | 51.30 | 44.30 | 0.50 | — | 0.50 | 3.40 |
| 19 | 4-PcNox | 1:2 | DMP+MeOH | 97.5 | 800 | 60 | 98.90 | 45.00 | 52.00 | 2.60 | — | — | 2.40 |
| 20[3] | 4-PcNox | 1:2 | MeOH | 97.5 | 800 | 60 | 100.00 | 54.50 | 38.70 | 2.00 | — | 2.00 | — |
| 21 | 4-PcNox | 1:2 | Benzene+MeOH | 97.5 | 800 | 60 | 79.88 | 34.23 | 53.70 | 6.74 | — | 0.52 | 4.8 |
| 22 | 4-PcNox | 2:1 | MeOH | 97.5 | 800 | 90 | 100.00 | 40.20 | 45.20 | 1.98 | — | 12.00 | 0.30 |
| 23 | 4-PcNox | 1:4 | MeOH | 97.5 | 800 | 90 | 100.00 | 51.75 | 43.54 | 1.46 | — | 0.80 | — |
| 24 | 4-PcNox | 1:8 | DMP+MeOH | 97.5 | 800 | 115 | 99.90 | 67.70 | 21.60 | — | — | 0.62 | 10.10 |
| 25 | 4-PcNox | 2:1 | MeOH | 97.5 | 800 | 120 | 100.00 | 40.40 | 47.50 | 2.40 | — | 8.72 | 0.57 |
| 26 | 4-PcNox | 1:2 | MeOH | 97.5 | 800 | 120 | 86.80 | 57.80 | 29.50 | 5.20 | — | 3.60 | 1.30 |
| 27 | 4-PcNox | 1:16 | DMP+MeOH | 97.5 | 800 | 120 | 16.20 | 64.80 | — | — | — | 0.25 | 34.90 |
| 28 | 4-PcNox | 1:8 | ADN+MeOH | 97.5 | 800 | 150 | 22.60 | 53.70 | 20.70 | — | — | — | 25.60 |
| 29 | 4-PcNox | 1:1 | ADN+MeOH | 97.5 | 800 | 180 | 84.40 | 68.90 | 23.50 | 2.00 | — | 2.30 | 3.30 |
| 30[1] | 4-PcNox | 1:2 | MeOH | 97.5 | 800 | 180 | 100.00 | 56.30 | 39.60 | 1.29 | — | 1.13 | 0.20 |
| 31[4] | 4-PcNox | 1:2 | MeOH | 97.5 | 800 | 180 | 48.10 | 9.73 | — | — | — | — | 84.20 |
| 32[5] | 4-PcNox | 1:2 | MeOH | 97.5 | 800 | 180 | 93.40 | 22.90 | 74.00 | 1.50 | — | — | — |
| 33[6] | 4-PcNox | 1:2 | MeOH | 97.5 | 800 | 180 | 100.00 | 48.90 | 48.00 | 1.20 | — | 0.30 | 0.80 |
| 34[4] | 4-PcNox | 1:2 | DMP+MeOH | 97.5 | 800 | 180 | 91.10 | 39.90 | 53.90 | Trace | — | 0.40 | 5.30 |
| 35 | 4-PcNox | 1:8 | MeOH | 97.5 | 800 | 180 | 100.00 | 36.90 | 60.60 | 1.01 | — | 0.25 | 0.50 |
| 36 | 4-PcNox | 1:16 | MeOH | 97.5 | 800 | 180 | 100.00 | 26.80 | 48.30 | 10.46 | — | — | 14.33 |
| 37 | 4-PcNox | 1:2 | MeOH | 97.5 | 800 | 225 | 100.00 | 30.90 | 61.90 | 1.00 | — | 3.50 | 2.70 |
| 38[7] | 4-PcNox | 1:2 | MeOH | 97.5 | 800 | 300 | 53.70 | 57.00 | 39.00 | — | — | 2.40 | 1.00 |
| 39 | 4-PcNox | 1:4 | MeOH | 115 | 800 | 120 | 100.00 | 56.93 | 37.52 | 1.43 | — | 3.13 | — |
| 40 | 4-PcNox | 1:2 | DMP+MeOH | 117.5 | 800 | 10 | 87.70 | 67.00 | 18.70 | 4.20 | — | 0.20 | 9.90 |
| 41 | 4-PcNox | 1:2 | DMP+MeOH | 117.5 | 800 | 60 | 100.00 | 52.40 | 38.20 | 1.90 | — | 2.80 | 4.60 |
| 42 | 4-PcNox | 1:2 | MeOH | 125 | 800 | 180 | 100.00 | 49.30 | 40.00 | 4.48 | — | 4.49 | — |
| 43 | 4-PcNox | 1:2 | MeOH | 97.5 | 700 | 50 | 100.00 | 57.00 | 35.50 | 0.80 | — | 5.20 | 1.50 |
| 44 | 4-PcNox | 1:2 | ADN+MeOH | 97.5 | 600 | 150 | 57.60 | 99.80 | — | — | — | — | 0.20 |
| 45 | 4-PcNox | 1:2 | MeOH | 97.5 | 600 | 180 | 100.00 | 56.30 | 37.80 | 2.01 | — | 2.21 | 1.15 |
| 46 | 4-PcNox | 1:2 | DMP+MeOH | 97.5 | 500 | 120 | 99.70 | 55.90 | 40.30 | 1.50 | — | 0.60 | — |
| 47[8] | 4-PcNox | 1:2 | DMP+MeOH | 85 | 400 | 170 | 74.60 | 60.80 | 35.10 | — | — | — | 3.90 |
| 48[8] | 4-PcNox | 1:2 | DMP+MeOH | 85 | 400 | 420 | 97.30 | 51.50 | 38.40 | 0.90 | — | 3.60 | 3.41 |
| 49 | 4-PcNox | 1:2 | DMP+MeOH | 97.5 | 400 | 25 | 88.20 | 73.70 | 17.70 | 2.80 | — | — | 5.80 |
| 50 | 4-PcNox | 1:4 | DMP+MeOH | 97.5 | 400 | 25 | 51.51 | 82.36 | 7.95 | — | — | — | 9.13 |
| 51 | 4-PcNox | 1:2 | DMP+MeOH | 97.5 | 400 | 40 | 97.30 | 70.90 | 21.30 | 2.10 | — | 0.40 | 5.30 |
| 52 | 4-PcNox | 1:4 | DMP+MeOH | 97.5 | 400 | 50 | 76.03 | 88.95 | 3.66 | — | — | — | 6.99 |
| 53 | 4-PcNox | 1:2 | DMP+MeOH | 97.5 | 400 | 60 | 100.00 | 62.90 | 29.70 | 2.10 | — | 0.80 | 4.40 |
| 54 | 4-PcNox | 1:4 | DMP+MeOH | 97.5 | 400 | 60 | 67.95 | 81.56 | 11.36 | — | — | — | 6.68 |
| 55 | 4-PcNox | 1:4 | DMP+MeOH | 97.5 | 400 | 150 | 91.95 | 81.01 | 11.16 | 0.81 | — | — | 6.67 |
| 56[8] | 4-PcNox | 1:2 | DMP+MeOH | 97.5 | 400 | 180 | 49.70 | 92.30 | 0.10 | — | — | — | 5.32 |
| 57 | 4-PcNox | 1:2 | DMP+MeOH | 97.5 | 400 | 285 | 55.70 | 89.27 | 0.63 | 5.35 | — | — | 4.53 |
| 58 | 4-PcNox | 1:2 | DMP+MeOH | 97.5 | 400 | 300 | 62.12 | 86.80 | 0.73 | 5.42 | — | 1.53 | 4.61 |
| 59 | 4-PcNox | 1:8 | DMP+MeOH | 117.5 | 400 | 120 | 47.50 | 74.56 | 0.17 | — | — | 0.23 | 19.95 |
| 60 | 4-PcNox | 1:2 | DMP+MeOH | 97.5 | 300 | 15 | 69.70 | 89.90 | — | 4.30 | — | 0.70 | 5.00 |
| 61 | 4-PcNox | 1:2 | DMP+MeOH | 97.5 | 300 | 20 | 24.40 | 86.90 | — | — | — | — | 5.00 |
| 62 | 4-PcNox | 1:1 | DMP+MeOH | 97.5 | 300 | 25 | 85.60 | 87.60 | — | 6.80 | — | — | 5.70 |
| 63 | 4-PcNox | 1:2 | DMP+MeOH | 97.5 | 300 | 25 | 46.80 | 93.80 | — | — | — | — | 6.20 |
| 64 | 4-PcNox | 1:2 | DMP+MeOH | 97.5 | 300 | 30 | 80.40 | 90.10 | — | 3.60 | — | — | 6.31 |
| 65 | 4-PcNox | 1:2 | DMP+MeOH | 97.5 | 300 | 50 | 59.80 | 91.90 | — | 2.60 | — | — | 5.20 |
| 66 | 4-PcNox | 1:2 | DMP+MeOH | 97.5 | 300 | 60 | 66.30 | 94.00 | — | 0.20 | — | — | 5.80 |
| 67 | 4-PcNox | 1:2 | DMP+MeOH | 97.5 | 300 | 70 | 72.70 | 94.20 | Trace | — | — | — | 5.80 |
| 68 | 4-PcNox | 1:2 | DMP+MeOH | 97.5 | 300 | 90 | 79.10 | 91.70 | Trace | 2.30 | — | 0.40 | 5.60 |
| 69 | 4-PcNox | 1:2 | DMP+MeOH | 97.5 | 300 | 120 | 81.20 | 92.30 | Trace | 2.10 | — | 0.30 | 5.30 |
| 70 | 4-PcNox | 1:2 | DMP+MeOH | 97.5 | 300 | 140 | 88.70 | 92.50 | Trace | 2.10 | — | 0.60 | 4.80 |
| 71 | 4-PcNox | 1:2 | DMP+MeOH | 97.5 | 300 | 150 | 91.90 | 79.80 | 10.20 | 2.30 | — | — | 4.60 |
| 72 | 4-PcNox | 1:8 | DMP+MeOH | 97.5 | 300 | 150 | 85.70 | 91.80 | 3.30 | — | — | — | 4.90 |
| 73 | 4-PcNox | 1:1 | DMP+MeOH | 97.5 | 300 | 180 | 91.10 | 72.20 | 18.20 | 5.30 | — | — | 4.30 |
| 74 | 4-PcNox | 1:2 | DMP+MeOH | 97.5 | 300 | 180 | 99.50 | 76.80 | 16.90 | 2.00 | — | 0.20 | 4.20 |

TABLE I-continued
CARBONYLATION WITH HETEROCYCLIC NITROGEN COMPOUNDS

Catalyst: Co$_2$(CO)$_8$ + Ligand
Unsaturated Olefin Feed: Acrylonitrile

| Example | Ligand | Co$_2$(CO)$_8$/Ligand | Solvent | Temp (°C.) | Pres (psi) | Time (min) | Conv (%) | Yields (%) | | | | | |
|---|---|---|---|---|---|---|---|---|---|---|---|---|---|
| | | | | | | | | 3-CE | 2-CE | PN | 3-CPA | 3-CPAA | 3-MPN |
| 75 | 4-PcNox | 1:2 | DMP+MeOH | 117.5 | 300 | 25 | 58.80 | 82.40 | — | 9.70 | — | — | 7.90 |
| 76 | 4-PcNox | 1:1 | DMP+MeOH | 117.5 | 300 | 120 | 38.44 | 77.32 | — | 11.57 | — | — | 5.75 |
| 77 | 4-PcNox | 1:8 | DMP+MeOH | 117.5 | 300 | 120 | 45.30 | 78.60 | — | 11.60 | — | — | 7.50 |
| 78 | 4-PcNox | 1:2 | DMP+MeOH | 117.5 | 300 | 150 | 63.30 | 80.70 | — | 8.30 | — | 0.30 | 10.80 |
| 79 | 4-PcNox | 1:4 | DMP+MeOH | 117.5 | 300 | 180 | 87.40 | 93.40 | 6.00 | — | — | — | 0.50 |
| 80 | 4-PcNox | 1:8 | DMP+MeOH | 117.5 | 300 | 180 | 48.20 | 69.60 | — | 13.20 | — | — | 3.60 |
| 81 | PyNox | 1:2 | MeOH | 95 | 800 | 60 | 100.00 | 31.58 | 62.38 | 2.14 | — | 3.54 | 0.06 |
| 82 | PyNox | 1:2 | MeOH | 97.5 | 800 | 180 | 100.00 | 52.40 | 42.20 | 1.50 | — | 3.10 | — |
| 83 | 2-PcNox | 1:2 | MeOH | 95 | 800 | 120 | 87.03 | 8.99 | 78.75 | 2.13 | 3.43 | 2.71 | 0.32 |
| 84 | 4-MPyNox | 1:2 | MeOH | 95 | 800 | 90 | 100.00 | 45.68 | 51.96 | 0.91 | — | 0.99 | 0.19 |
| 85 | 4-MPyNox | 1:2 | DMP+MeOH | 97.5 | 400 | 20 | 61.13 | 84.07 | 10.00 | 2.16 | — | — | — |
| 86 | 4-MPyNox | 1:2 | DMP+MeOH | 97.5 | 800 | 10 | 69.40 | 65.50 | 30.50 | — | — | 4.00 | — |
| 87 | 4-MPyNox | 1:2 | DMP+MeOH | 97.5 | 800 | 20 | 94.30 | 55.50 | 41.00 | 1.00 | — | 2.50 | — |
| 88 | 4-MPyNox | 1:4 | MeOH | 97.5 | 800 | 90 | 97.40 | 34.50 | 62.30 | 0.99 | — | 0.28 | 2.10 |
| 89 | 4-MPyNox | 1:16 | MeOH | 97.5 | 800 | 180 | 71.30 | 19.80 | 72.90 | 2.84 | — | — | 1.37 |
| 90 | Pc acid | 1:2 | MeOH | 97.5 | 800 | 180 | 42.30 | 24.10 | — | — | — | 6.90 | 23.50 |
| 91 | 3-Py Carb | 1:2 | DMP+MeOH | 97.5 | 800 | 15 | 57.70 | 69.10 | 30.90 | — | — | — | — |
| 92 | 3-Py Carb | 1:2 | DMP+MeOH | 97.5 | 800 | 30 | 95.20 | 41.90 | 46.30 | 0.90 | 6.70 | 4.20 | — |
| 93 | 3-Py Carb | 1:2 | MeOH | 97.5 | 800 | 180 | 100.00 | 40.50 | 52.80 | 1.95 | — | 4.40 | 0.03 |
| 94 | QuNox | 1:2 | MeOH | 97.5 | 800 | 180 | 100.00 | 1.09 | 93.30 | — | 0.67 | 4.58 | 0.07 |
| 95 | t-but PyNox | 1:2 | DMP+MeOH | 97.5 | 800 | 25 | 81.40 | 58.30 | 28.40 | — | — | — | — |
| 96 | t-but PyNox | 1:2 | DMP+MeOH | 97.5 | 800 | 60 | 100.00 | 40.80 | 51.50 | 0.20 | — | — | — |
| 97[1] | t-but PyNox | 1:2 | MeOH | 97.5 | 800 | 180 | 100.00 | 50.50 | 46.80 | 1.30 | — | 0.60 | 0.30 |

[1] 2.2% H$_2$
[2] 10% H$_2$
[3] 2 × Cat. Conc.
[4] 0% H$_2$
[5] Preformed in 5% H$_2$; run on 0% H$_2$
[6] 1% H$_2$
[7] 1/10 × Cat. Conc.
[8] ½ Cat. Conc.

| COMPOUND NAME ABBREVIATIONS | |
|---|---|
| Abbreviation | Compound Name |
| ADN | adiponitrile |
| BiPy-Nox | bipyridyl-di-N—oxide |
| 2 CE | methyl-α-cyanopropionate |
| 3 CE | methyl-β-cyanopropionate |
| 3 CPA | 3-cyano-propionaldehyde |
| 3 CPAA | 3-cyano-propionaldehyde dimethyl acetal |
| DIABLO | diazabicyclo (2.2.2) octane |
| DMP | dimethylphthalate |
| DMSO | dimethyl sulfoxide |
| 3-MPN | 3-methoxy propionitrile |
| 4-MPyNox | 4-methoxy-pyridine-N—oxide |
| 4-NPyNox | 4-nitro-pyridine-N—oxide |
| Pc acid | picolinic acid-N—oxide |
| 2-PcNox | 2-picoline-N—oxide |
| 4-PcNox | 4-Picoline-N—oxide |
| PN | propionitrile |
| PVPYRL | polyvinylpyrrolidone |
| 3-Py Carb | 3-pyridylcarbinol-N—oxide |
| PyNox | pyridine-N—oxide |
| QuNox | quinoline-N—oxide, dihydrate |
| TAD | tetraazadecane |
| t-but PyNox | 4-t-butyl-pyridine-N—oxide |
| TEPO | triethyl phosphate oxide |
| TPPO | triphenylphosphine oxide |

EXAMPLE 101

In each of the above example, methanol was used as the compound containing a replaceable hydrogen atom.

In the following examples, either t-butyl alcohol or n-amyl alcohol were used in place of methanol.

13.5 gms. of acrylonitrile, 0.88 gms. of 4-picoline-N-oxide and 100 mls. of t-budyl alcohol were placed into a glasslined autoclave. Next, 1.37 gms. of Co$_2$(CO)$_8$ were added and the autoclave sealed.

The autoclave was charged with synthesis gas containing 5% H$_2$ to a pressure of 800 psi. The temperature was set at 97.5° C. and the reaction proceeded for 180 minutes. The glasslined autoclave was then brought to room temperature by cooling with cold water, depressurized and opened for product analysis. The product analysis is shown in Table II.

EXAMPLES 102 AND 103

These examples follow the same procedure outlined in Example 101 execpt that the solvent, alcohol and reaction time were varied. These variables and the product analysis are shown in Table II.

EXAMPLES 104

In each of the above examples the unsaturated olefin feed was acrylonitrile. In the following two examples, other olefins were fed to the inventive reaction system. 5.26 gms. of propylene, 0.88 gms. of 4-picoline-N-oxide, 8.15 gms. of methanol and 100 mls. of orthoxylene were placed into a glasslined autoclave. Next, 1.37 gms. of Co$_2$(CO)$_8$ were added and the autoclave sealed.

TABLE II
CARBONYLATION WITH HETEROCYCLIC NITROGEN LIGAND

Catalyst: $Co_2(CO)_8$ + Ligand
Unsaturatd Olefin Feed: Acrylonitrile

| Example | Ligand | $Co_2(CO)_8$/Ligand | Solvent | Temp (°C.) | Pres (psi) | Time (min) | Conv (%) | Yields (%) 3-CE | 2-CE | PN | 3-CPA | 3-CPAA | 3-MPN |
|---|---|---|---|---|---|---|---|---|---|---|---|---|---|
| 101 | 4-PcNox | 1:2 | t-but alcohol | 97.5 | 800 | 180 | 100.00 | 1.80 | 94.90 | 1.50 | 0.75 | — | — |
| 102 | 4-PcNox | 1:2 | ADN + t-but alcohol | 97.5 | 800 | 150 | 43.72 | — | 87.39 | — | — | — | — |
| 103 | 4-PcNox | 1:2 | ADN + n-amyl alcohol | 97.5 | 800 | 180 | 55.62 | 39.70 | 0.61 | 1.99 | — | 0.68 | 10.19 | was set at 97.5° C. and the reaction proceeded for 180 minutes. The glasslined autoclave was then brought to room temperature by cooling with cold water, depressurized and opened for product analysis. An 80% conversion of propylene was obtained with a 56% yield of N-methylbutyrate and a 20% yield of methyl iso-butyrate.

EXAMPLE 105

14.8 gms. of alkyl alcohol, 1.45 gms. of quinoline-N-oxide and 100 mls. of t-butyl alcohol were placed into a glasslined autoclave. Next, 1.37 gms. of $Co_2(CO)_8$ were added and the autoclave sealed.

The autoclave was charged with synthesis gas containing 5% $H_2$ to a pressure of 800 psi. The temperature was set at 97.5° C. and the reaction proceeded for 180 minutes. The glasslined autoclave was then brought to room temperature by cooling with cold water, depressurized and opened for product analysis. A 100% conversion of allyl alcohol was obtained with a 50% yield of propionaldehyde and a 50% yield of butyrolactone.

EXAMPLE 106

Each of the above examples used a heterocyclic nitrogen ligand. The following examples use phosphorus or sulfur oxide ligands. 13.5 gms. of acrylonitrile, 1.46 gms. of triethylphosphateoxide and 100 mls. of methanol were placed into a glass lined autoclave. Next, 1.37 gms. of $Co_2(CO)_8$ were added and the autoclave sealed.

The autoclave was charged with synthesis gas containing 5% $H_2$ to a pressure of 800 psi. The temperature ws set at 95° C. and the reaction proceeded for 180 minutes. The glasslined autoclave was then brought to room temperature by cooling with cold water, depressurized and opened for product analysis. The product analysis is shown in Table III.

EXAMPLES 107 THRU 109

The procedure outlined in Example 106 was followed with the temperature, reaction time and ligand being varied. These variables and the product analysis are shown in Table III.

TABLE III
CARBONYLATION WITH PHOSPHORUS OR SULFUR ALKYL OXIDES

Catalyst: $Co_2(CO)_8$ + Ligand
Unsaturated Olefin Feed: Acrylonitrile

| Example | Ligand | $Co_2(CO)_8$/Ligand | Solvent | Temp (°C.) | Pres (psi) | Time (min) | Conv (%) | Yields (%) 3-CE | 2-CE | PN | 3-CPA | 3-CPAA | 3-MPN |
|---|---|---|---|---|---|---|---|---|---|---|---|---|---|
| 106 | TEPO | 1:2 | MeOH | 95 | 800 | 180 | 65.30 | 4.87 | 64.50 | 9.60 | — | 9.39 | — |
| 107 | DMSO | 1:2 | MeOH | 95 | 800 | 180 | 64.10 | 3.83 | 57.70 | 10.84 | — | 12.70 | 2.73 |
| 108 | TPPO | 1:2 | MeOH | 115 | 800 | 90 | 57.20 | 4.81 | 44.30 | 18.70 | — | 8.56 | 10.50 |
| 109 | TPPO | 1:2 | MeOH | 95 | 800 | 240 | 76.70 | 6.05 | 72.70 | 7.70 | — | 7.05 | 9.13 |

As is shown in the above examples, the use of heterocyclic nitrogen oxide compounds and phosphorus and sulfur oxide compounds results in the promotion of cobalt and ruthenium carbonyl catalysts to permit the production of oxygenated organic compounds from the olefinically unsaturated compounds and compounds having a replaceable hydrogen atom as set forth in the specification above. The above examples are not intended to limit the scope of the present invention, but have been provided merely to demonstrate operability.

Within the scope of the present invention, olefinically unsaturated compounds are those compounds having at least one non-aromatic carbon to carbon double bond and includes compounds having other functional groups such as alkyl, nitrile, carboxy, carbonyl, hydroxy, alkoxy, ester, halide, aryl and the like, provided that the groups do not adversely effect the carbonylation reaction. The olefinically unsaturated compound may be employed in the process of the invention as both reactant and solvent.

Within the scope of the present invention, oxygenated organic compounds are meant to include those compounds which are derived from the olefinically unsaturated compound via the carbonylation reaction and with contain a C-O or C=O group. Oxygenated organic compounds thus defined include, but are not limited to acids, esters, aldehydes, acetals, amides, and the cyano derivatives thereof.

The selection of metal carbonyl catalysts, promoters, olefinically unsaturated compounds, compounds containing a replaceable hydrogen atom, solvents and reactions conditions can be determined from the total specification disclosure provided without departing from the spirit of the invention herein disclosed and described, the scope of the invention including modifications and variations that fall within the scope of the attached claims.

We claim:

1. A process for the production of an oxygenated organic compound containing a nitrogen moiety wherein the straight chain product predominates comprising contacting an olefinically unsaturated compound in the liquid phase with carbon monoxide and a compound containing a replaceable hydrogen atom at a temperature of about 50° C. to about 150° C. in the presence of a catalyst comprising at least one of cobalt carbonyl and ruthenium carbonyl and a promoter ligand represented by the following structure:

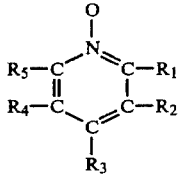

wherein $R_1$, $R_2$, $R_3$, $R_4$, and $R_5$ are each independently selected from the group consisting of:
(1) H;
(2) $C_{1-10}$ alkyls;
(3) $(CH_2)_q$ OH wherein q is 0–10;
(4)

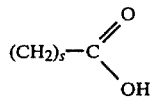

wherein s is 0–10; and
(5) $O(CH_2)_t CH_3$ wherein t is 0–10; and
wherein $R_1$ and $R_2$ may comprise a five to eight membered carbocyclic fused ring optionally substituted with $C_{1-10}$ alkyls;
wherein the compound containing a replaceable hydrogen atom is represented by the following formula:

H—Y wherein Y is selected from the group consisting of:
(1) $OR_{14}$ wherein $R_{14}$ is a $C_{1-30}$ alkyl;
(2)

wherein $R_{15}$ and $R_{16}$ are each independently selected from $C_{1-10}$ alkyls; and
(3) H;
wherein the olefinically unsaturated compound has the following structure:

$R_{11}CH=CHR_{12}$ wherein $R_{11}$ and $R_{12}$ are each independently selected from:
(1) hydrogen (either $R_{11}$ or $R_{12}$ but not both);
(2) $C_{1-30}$ alkyl;
(3) —$(CH_2)_p$—CN, wherein p is 0–3: and
(4) —$(CH_2)_q$—$OR_{13}$, wherein q is 1–30 and $R_{13}$ is hydrogen, methyl, or ethyl; and
(5) —$(CH_2)_n$—$COOR_{17}$, wherein n is 0.5 and $R_{17}$ is hydrogen, methyl or ethyl, with the proviso that at least one of $R_{11}$ and $R_{12}$ contains a nitrile moiety; and, wherein the molar ration of the compound containing a replaceable hydrogen atom to the olefinically unsaturated compound is 0.5:1 to 100:1.

2. The process of claim 1 wherein Y is selected from the group consisting of:
(1) $OR_{14}$ wherein $R_{14}$ is a $C_{1-10}$ alkyl;
(2)

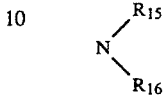

wherein $R_{15}$ and $R_{16}$ are each independently selected from $C_{1-14}$ alkyls; and
(3) H.

3. The process of claim 2 wherein the compound containing a replaceable hydrogen atom is selected from the group consisting of methanol, ethanol, propanol and butanol.

4. The process of claim 3 wherein the compound containing a replaceable hydrogen atom is methanol.

5. The process of claim 2 wherein the compound containing a replaceable hydrogen atom is $H_2$.

6. The process of claim 5 wherein the $H_2$ comprises 10% to 60% by volume of the total amount of carbon monoxide and $h_2$ in the reaction system.

7. The process of claim 6 wherein the $H_2$ comprises about 50% by volume of the total amount of carbon monoxide and $H_2$ in the reaction system.

8. The process of claim 1 wherein Y is selected from the group consisting of:
(1) $OR_{14}$ wherein $R_{14}$ is a $C_{1-30}$ alkyl; and
(2)

wherein $R_{15}$ and $R_{16}$ are each independently selected from $C_{1-10}$ alkyls.

9. The process of claim 8 wherein $H_2$ is present in the reaction system.

10. The process of claim 9 wherein the $H_2$ comprises less than 10% by volume of the total amount of carbon monoxide and $H_2$ in the reaction system.

11. The process of claim 10 wherein the $H_2$ comprises 0.5% to 7.5% by volume of the total amount of carbon monoxide and $H_2$ in the reaction system.

12. The process of claim 1 wherein $R_{11}$ and $R_{12}$ are each independently selected from:
(1) hydrogen (either $R_{11}$ or $R_{12}$ but not both;
(2) $C_{1-10}$ alkyl;
(3) —$(CH_2)_p$—CN, wherein p is 0–2; and
(4) —$(CH_2)_q$—OH, wherein q is 1–10 with the proviso that at least one of $R_{11}$ and $R_{12}$ contains a nitrile moiety.

13. The process of claim 12 wherein $R_{11}$ and $R_{12}$ are each independently selected from:
(1) hydrogen (either $R_{11}$ or $R_{12}$ but not both);
(2) methyl; and
(3) —$(CH_2)_p$—CN, wherein p is 0–1 with the proviso that at least one of $R_{11}$ and $R_{12}$ contains a nitrile moiety.

14. The process of claim 1 wherein the olefinically unsaturated compound is selected from the group consisting of acrylonitrile, and pentenenitrile.

15. The process of claim 14 wherein the olefinically unsaturated compound is acrylonitrile.

16. The process of claim 1 wherein the process is conducted in the presence of an inert organic solvent.

17. The process of claim 1 wherein the process is conducted in the presence of an organic solvent comprising at least one of the reactant olefinically usaturated compounds or compounds having a replaceable hydrogen atom.

18. The process of claim 1 wherein the process is conducted in the presence of a solvent selected from the group consisting of a alcohol, aromatic, ester, nitrile and dinitrile.

19. The process of claim 18 wherein the solvent is an alcohol or ester.

20. The process of claim 1 wherein the molar ratio of the compound containing a replaceable hydrogen atom to the olefinically unsaturated compound is about 1:1 to about 10:1.

21. The process of claim 1 wherein the catalyst contains cobalt carbonyl.

* * * * *